United States Patent

Maxwell et al.

[11] Patent Number: 5,831,185
[45] Date of Patent: Nov. 3, 1998

[54] METHOD AND APPARATUS FOR COLLECTING SAMPLES OF EARTH MATERIALS

[75] Inventors: Gary S. Maxwell, Edmonds; Clifford J. Whitmus, Jr., Marysville; K. Michael McDowell, Seattle, all of Wash.

[73] Assignee: Pentec Technologies, Inc., Edmonds, Wash.

[21] Appl. No.: 743,950

[22] Filed: Nov. 5, 1996

[51] Int. Cl.$^6$ .................................................. G01N 1/08
[52] U.S. Cl. ...................................... 073/864.45; 175/20
[58] Field of Search .................. 73/864.44, 864.45, 73/170.32; 175/20, 58, 56

[56] References Cited

U.S. PATENT DOCUMENTS

| | | | |
|---|---|---|---|
| 2,340,738 | 2/1944 | Dilley | 255/4 |
| 2,665,885 | 1/1954 | Gignoux | 255/1.4 |
| 3,155,174 | 11/1964 | Niskin | 175/4 |
| 3,345,879 | 10/1967 | Nasu et al. | 73/425.2 |
| 3,940,982 | 3/1976 | Hironaka | 73/170 |
| 4,166,508 | 9/1979 | van den Berg | 175/20 |
| 4,345,461 | 8/1982 | Lezgintsev et al. | 73/170.32 |
| 4,996,887 | 3/1991 | Voll et al. | 73/864.44 |
| 5,417,290 | 5/1995 | Barrow | 175/22 |
| 5,474,141 | 12/1995 | Hart | 73/864.44 |
| 5,488,876 | 2/1996 | Casey et al. | 73/864.45 |

FOREIGN PATENT DOCUMENTS

| | | | |
|---|---|---|---|
| 2 420 131 | 3/1978 | France . | |
| 815564 A | 2/1979 | U.S.S.R. . | |
| 1111053 A | 8/1984 | U.S.S.R. . | |
| 1681176 | 9/1991 | U.S.S.R. | 73/864.45 |

*Primary Examiner*—Hezron E. Williams
*Assistant Examiner*—Nashmiya Fayyaz
*Attorney, Agent, or Firm*—Seed and Berry LLP

[57] ABSTRACT

A sampling method and apparatus especially suited for collecting under water samples of an earth material is disclosed. An open ended sample container is driven into an earth material body with a linear force while the transverse vibrations are provided to aid sample collection. The sample container is vibrated by reciprocally driving the sample container back and forth substantially transversely to a first direction in which the sample container is driven into the earth material body. After sample collection, the sample container and sample are removed from the earth material body by reciprocally driving the sample container back and forth transversely to the first direction while applying to the sample container a linear force directed opposite to the first direction.

8 Claims, 3 Drawing Sheets

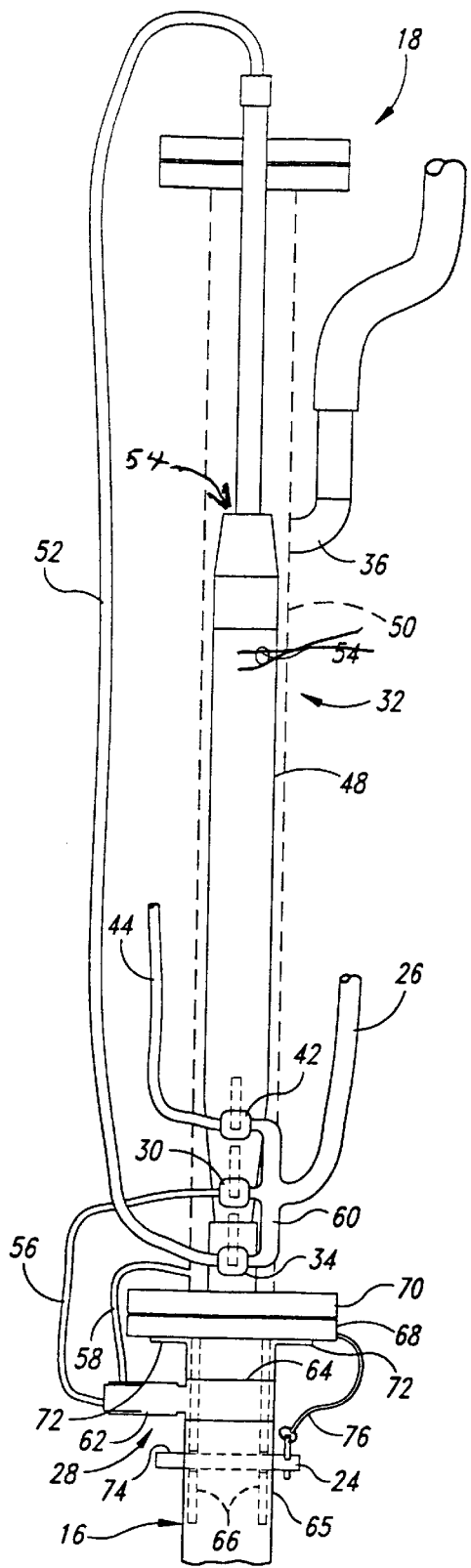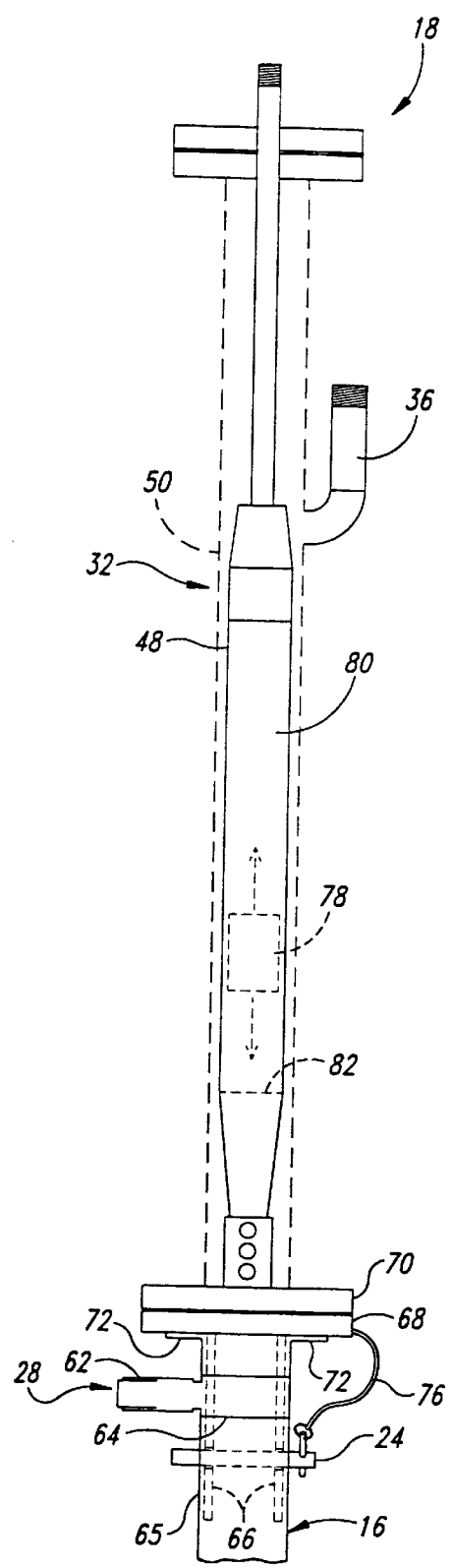
*Fig. 2*  *Fig. 3*

METHOD AND APPARATUS FOR COLLECTING SAMPLES OF EARTH MATERIALS

TECHNICAL FIELD

The present invention relates to environmental analysis, and more particularly, to collecting samples of earth materials for analysis.

BACKGROUND OF THE INVENTION

It is often necessary or desirable to determine the chemical composition of earth materials such as soils or sediments. The reasons for such chemical analysis include mineral and fossil fuel exploration, scientific pursuits, and satisfaction of environmental regulations. Typically, such chemical analysis requires samples of the earth materials to be collected in the field and taken to a laboratory for the analysis.

One common method of obtaining samples of earth materials employs heavy earthmoving equipment such as hydraulic shovels. Such hydraulic shovels typically scoop up a large quantity (approximately 1–2 cubic yards) of earth material and carry the earth material to a person who manually transfers portions of the earth material into sampling containers that are taken to a laboratory for analysis. One problem with such hydraulic shovel samplers is that much manual labor is involved in transferring the earth materials to the sample containers. Another problem is that the transfer may allow contaminants to be mixed with the earth material to be analyzed. In addition, it is difficult to prevent earth materials that were at different depths in the ground from being mixed together when scooping and transferring the earth material when using such hydraulic shovel samplers.

Another common sampling method employs devices known as core samplers which force a sampling container known as a core tube directly into the earth material being sampled. One such prior core sampler employs a hydraulic hammer that pounds the core tube into the earth material. Such a hydraulic hammer core sampler weighs approximately one ton and requires a gantry or ship (for underwater applications) to support the core sampler and enable it to force the core tube into the earth material. As a result, the hydraulic hammer core sampler cannot be employed to obtain samples of earth material located underneath docks, piers, or other obstacles. In addition, such hydraulic hammer core samplers typically are relatively slow—requiring up to 20 minutes to obtain a single sample.

Another prior art core sampler, known as a Vibra-Core, employs two electric motors to drive the core tube into the earth material. The Vibra-Core sampler reciprocally shakes the core tube vertically up and down to work the core tube into the earth material. The Vibra-Core sampler is relatively slow and inefficient because the entire core tube is moved upward and downward.

For underwater applications, a disadvantage to both the hydraulic hammer core sampler and the Vibra-Core sampler is that they must be deployed directly beneath a sampling ship's lifting apparatus and thus cannot be easily employed to obtain samples underneath obstacles such as piers.

SUMMARY OF THE INVENTION

The present invention is directed to a method and apparatus for collecting a sample of an earth material in a sample container having an end with an opening. In a preferred embodiment, the method orients the sample container so that the end with the opening is directed toward a body of earth material. The sample container is driven into the earth material body with a linear force directed in a first direction toward the earth material body. The sample container is vibrated while driving the sample container into the earth material body until the sample of earth material is collected in the sample container. The sample container is vibrated by reciprocally driving the sample container back and forth substantially transversely to the first direction. Preferably the sample container and the sample are removed from the body of earth material by continuing to reciprocally drive the sample container back and forth transversely to the first direction while applying to the sample container a linear force directed away from the earth material body. The earth material being sampled can include soils and other materials on dry land as well as sediments and other materials under water.

BRIEF DESCRIPTION OF THE DRAWINGS

FIG. 2 is a partial cutaway, side elevational view of a driving apparatus employed in the sampling apparatus shown in FIG. 1.

FIG. 3 is a partial cutaway, side elevational view of the driving apparatus shown in FIG. 2.

DETAILED DESCRIPTION OF THE INVENTION

Figure 1:
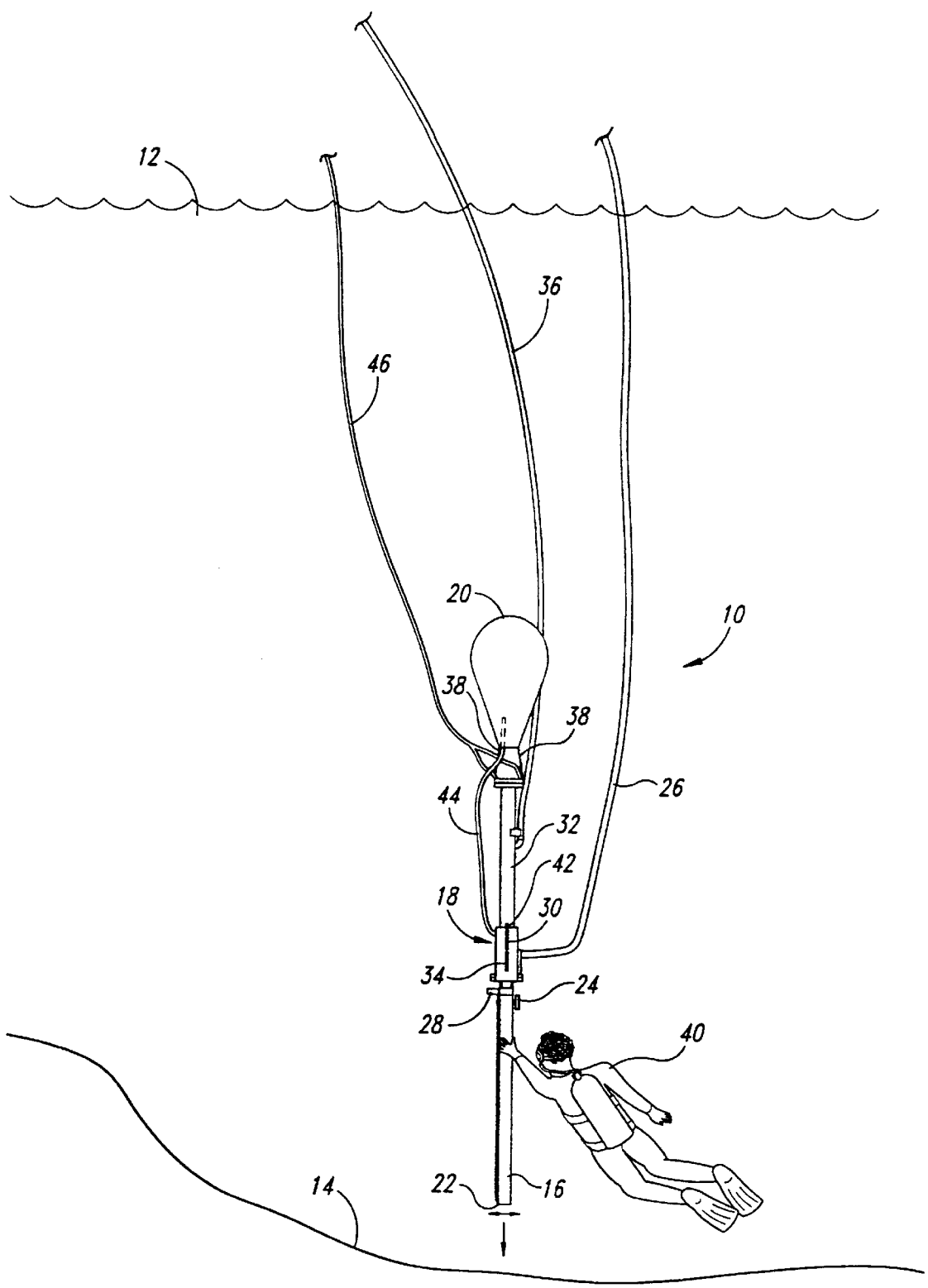
FIG. 1 is a side elevational view of a sampling apparatus being deployed according to a preferred embodiment of the present invention.

A sampling apparatus 10 for collecting samples of earth material according to a preferred embodiment of the present invention is shown in FIG. 1. In the embodiment shown in FIG. 1, the sampling apparatus 10 is deployed within a body of water 12 to collect sediment samples from a sediment floor 14 of the body of water 12. Alternatively, the sampling apparatus 10 can be employed to collect earth materials other than sediments, such as soils.

The sampling assembly 10 includes three main elements: a core tube 16, a driver assembly 18, and a lift bag 20. In the preferred embodiment shown in FIG. 1, the core tube 16 is an elongated hollow box having a rectangular cross-section and a bottom opening 22 through which sediment enters the core tube when the core tube is driven into the sediment floor 14 by the driver assembly 18. For example, the core tube 16 may have a cross-sectional size of 4×4 inches and a length ranging from 5 to 21 feet. Alternatively, the core tube 16 could be cylindrical or other shapes and still be efficiently driven into the sediment floor 14 by the driver assembly 18. The core tube 16 is releasably coupled to the driver assembly 18 by a releasable pin 24, as shown in more detail in FIGS. 2 and 3.

In contrast to prior art sediment samplers, the driver assembly 18 is structured to drive the core tube 16 into the sediment floor 14 with both a linear force directed in a first direction toward the earth material and a vibrational force that reciprocally drives the core tube 16 back and forth substantially perpendicular to the first direction. It has been found that a relatively low-amplitude, high-frequency vibration of the core tube 16 maximizes the amount of sediment that enters the core tube 16. It is believed that the vibration causes liquefaction of the sediment along the contact surface between the core tube 16 and the sediment floor 14, which reduces the friction between the core tube 16 and the sediment floor.

In the preferred embodiment shown in FIG. 1, the driver assembly 18 is actuated pneumatically by a supply of compressed air received via an air intake line 26 coupled to an air compressor on a sampling vessel (not shown). The driver assembly 18 includes a pneumatic vibrator 28 coupled to the air intake line 26 via a vibrator valve 30. The pneumatic vibrator 28 is mechanically coupled to the core tube 16 in order to impart the transverse vibrational force to the core tube 16 as discussed above. In the preferred embodiment, the vibrator 28 is implemented using a Vibrolator rotary vibrator (part number UCVR6.5) from Martin Engineering, Inc., although other commercial vibrators could also be employed.

The driver assembly 18 also includes a linear driver assembly 32 that drives the core tube 16 into the sediment floor 14 while the core tube 16 is being vibrated by the pneumatic vibrator 28. The linear driver assembly 32 is supplied with air from the air intake line 26 via a linear driver valve 34. The linear driver assembly 32 includes an air exhaust line 36 that releases exhaust air from the linear driver assembly.

In the preferred embodiment, the air exhaust line 36 is sufficiently long to reach the air surface above the body of water 12 so that the exhaust air is released above the body of water 12. Releasing exhaust air to the surface via the air exhaust line 36, rather than releasing the exhaust air directly into the body of water 12, provides at least two advantages. First, releasing the exhaust air directly into the body of water 12 would require the pressure in the air exhaust line 36 to be greatly increased to overcome the pressure caused by the weight of the body of water 12. In contrast, releasing the exhaust air to the surface via the air exhaust line 36 only requires that the air pressure in the exhaust line 36 exceeds the relatively low air pressure above the body of water 12. Second, releasing the exhaust air to the surface via the air exhaust line 36 reduces the possibility of contamination of the earth material sample from contact with the exhausted air which may contain lubricating oil from the air compressor.

The airbag 20 helps to support the core tube 16 and driver assembly 18 such that a diver 40 can move the sampling apparatus 10 to the position at which the earth material sample is being collected. The airbag 20 is coupled to the driver assembly 18 via airbag cables 38 and is provided with compressed air from the air intake line 26 via an airbag valve 42 and an airbag line 44. Forcing additional air into the airbag 20 will cause the airbag to help lift the sampling apparatus 10 out of the body of water 12. A connection cable 46 coupled between the driver assembly 18 and a winch (not shown) on the sampling vessel could also be employed to support the sampling assembly 10. Although the sampling assembly 10 could be raised and lowered solely using the winch and connection cable 46, the airbag 20 preferably is also used because the buoyancy of the airbag 20 is more easily controlled by the diver 40 using the airbag valve 42.

In the preferred embodiment, the entire sampling assembly 10 weighs less than approximately 250 pounds, so the diver 40 can easily position the sampling apparatus 10 in the desired sampling location with the assistance of the airbag 20. Moreover, the sampling apparatus 10 is connected to the sampling vessel using flexible air lines 26, 36 and a flexible connection cable 46, so the sampling apparatus can be deployed in areas where prior art sampling devices cannot, such as under floating docks. This contrasts with prior art sampling devices that are rigidly secured to a sampling vessel such that the prior art sampling devices can only be deployed directly underneath the sampling vessel.

A partial cutaway view of the driver assembly 18 is shown in FIG. 2. The linear driver assembly 32 includes a linear driver 48 positioned within a waterproof housing 50. In a preferred embodiment, the linear driver 48 is implemented using a Grundomat linear driver (part number 070769-37) from TT Technologies Inc. The linear driver 48 is coupled to the air intake line 26 via a linear driver line 52 and the linear driver valve 34. The compressed air received from the air intake line 26 via the linear driver line 52 and linear driver valve 34 is used by the linear driver 48 to drive the core tube 16 into the sediment floor 14 as discussed below with respect to FIG. 3. The linear driver 48 includes an air exhaust port 54 that allows exhaust air to be released to the interior of the waterproof housing 50 which releases the exhaust air via the air exhaust line 36.

The pneumatic vibrator 28 receives compressed air from the air intake line 26 via the vibrator valve 30 and a vibrator intake line 56. A vibrator exhaust line 58 coupled between the vibrator 28 and the waterproof housing 50 enables air to be released from the vibrator 28 to the interior of the waterproof housing 50. The air released into the waterproof housing 50 from the vibrator exhaust line 58 is released into the air exhaust line 36 along with the air exhausted from the linear driver 48. An intake manifold 62 couples the air intake line 26 to the vibrator valve 30, linear driver valve 34, and airbag valve 42, respectively, in order to supply the airbag 20, vibrator 28, and linear driver 48 with compressed air.

The pneumatic vibrator 28 includes a pneumatic motor 62 that vibrates a vibrator flange 64 abutting the core tube 16 when the compressed air is supplied to the vibrator 28. The vibrator flange 64 and a top end 65 of the core tube 16 each fit on a pair of parallel metal plates 66 that extend downwardly from a coupling plate 68 securely affixed to a support plate 70 of the waterproof housing 50. A pair of elbow connectors 72 securely couple the parallel plates 66 to the coupling plate 68. When the vibrator motor 62 vibrates the vibrator flange 64, the vibrations are transmitted via the parallel plates 66 to the core tube 16, thereby causing the core tube 16 to vibrate laterally. The lateral vibration of the core tube 16 assists the linear driver 48 in driving the core tube 16 into the sediment floor 14. Also, after the core tube 16 has been driven into the sediment floor 14 to a desired level, the lateral vibration assists the driver 40 in pulling the core tube 16 upward out of the sediment floor 14.

The releasable connecting pin 24 extends through opposite sides of the core tube 16 and through each of the parallel plates 66 to releasably couple the core tube 16 to the driver assembly 18 via the connecting plates 68, 70. The releasable connecting pin includes a spring-loaded detent 74 that holds the connecting pin 24 in place through the core tube 16 and parallel plates 66 until the connecting pin 24 is pulled sufficiently hard to overcome the retention by the spring-loaded detent 74 and thereby remove the connecting pin 24. Preferably the connecting pin 24 is securely attached to the connecting plate 68 by a retention line 76 to prevent the connecting pin from being lost after is it removed from the core tube 16 and parallel plates 66. After the connecting pin 24 is removed, the core tube 16 easily slides off of the parallel plates 66 and is replaced by another core tube.

FIG. 3 presents a similar view of the driver assembly 18 as FIG. 2 except with the air lines and air valves being removed for simplicity. In addition, FIG. 3 shows that the linear driver 48 includes a piston 78 within a hollow cylinder 80. When the diver 40 opens the linear driver valve 34, compressed air is forced into the top of the cylinder 80 via the linear driver air line 52. A valve system (not shown) within the cylinder 80 opens to allow the compressed air to impinge downwardly on the piston 78. The compressed air forces the piston 78 downwardly hard upon a base 82 like a hammer, which moves the entire driver assembly 18 downwardly and forces the core tube 16 into the sediment floor 14 (FIG. 1). After the piston 78 hammers the base 82, the valving system of the linear driver 48 automatically adjusts to force air onto a bottom surface of the piston 78 in order to force the piston to recoil upward. A small cushion of air is maintained above the piston 78 to cushion the upward movement of the piston 78 and thereby prevent the piston 78 from hammering the cylinder 80 upward. The valving system then changes again to force the air downward against the piston 78, which causes the piston 78 to drive the core tube 16 downward again. The entire process continues to repeat until the core tube 16 is driven a desired depth into the sediment floor 14.

When the core tube 16 has been driven a desired amount into the sediment core 14 to collect the sediment sample, the linear driver 48 is turned off by closing the linear driver valve 34 (FIG. 2). Then, the core tube 16 is pulled upwardly out of the sediment floor 14 by the diver 40, the lift bag 20, and/or the sampling vessel's winch (not shown) acting on the connecting cable 46. Preferably, the vibrator 28 is left running to assist in extracting the core tube 16 from the sediment floor 14. After the core tube 16 is extracted from the sediment floor 14, the vibrator 28 is turned off and the sampling assembly 10 is lifted out of the body of water 12 by the sampling vessel's winch.

Figure 4:
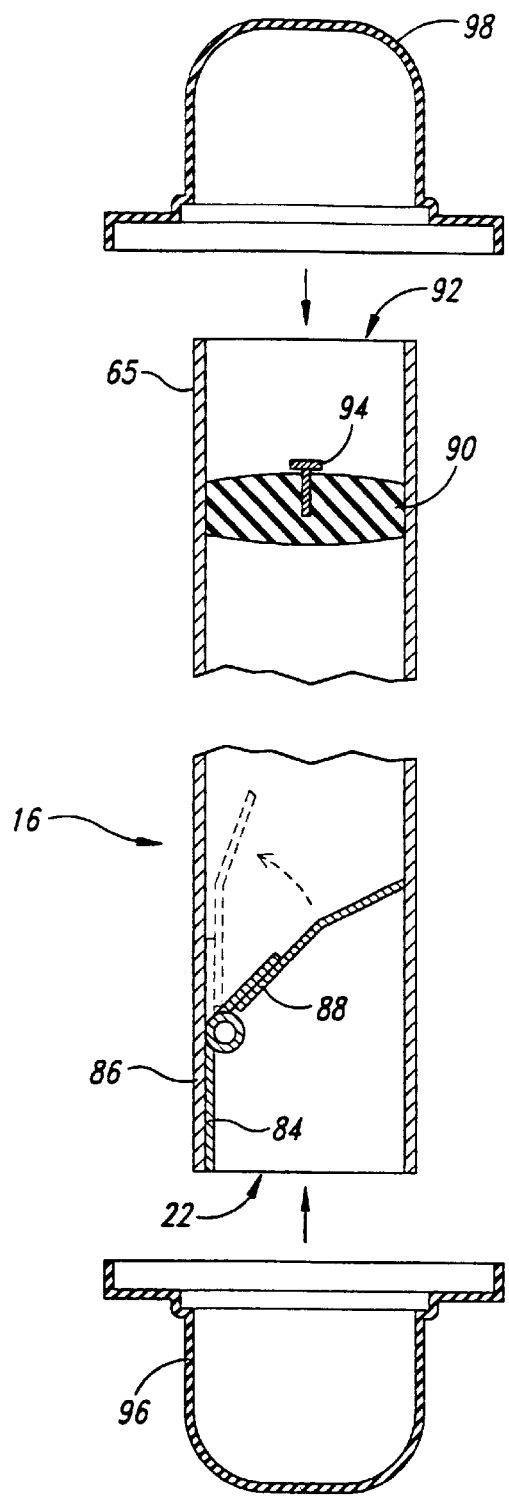
FIG. 4 is a cross-sectional view of a core tube of the sampling apparatus shown in FIG. 1.

A cross-sectional view of the core tube 16 is shown in FIG. 4. Attached to an inside wall 84 of a bottom end 86 of the core tube 16 is a hinged door 88 that releasably covers the bottom opening 22. As the core tube 16 penetrates the sediment floor 14, the sediment enters the bottom opening 22 and forces the hinged door open. As the core tube 16 continues to be forced into the sediment floor 14, the sediment entering the bottom opening 22 pins the hinged door 88 in an open position against the inside wall 84 of the core tube 16. After the sediment sample is collected in the core tube 16 and the core tube 16 begins being pulled out of the sediment floor 14, the hinged door 88 swings closed and thereby closes the bottom opening 22 of the core tube 16. As a result, the hinged door 88 prevents loss of the sediment sample collected as the core tube 16 is withdrawn from the sediment floor 14.

After the core tube 16 is removed from the sediment floor 14 and disconnected from the driver assembly 18, a rubber plug 90 is inserted into a top opening 92 in the top end 65 of the core tube 16. The rubber plug 90 is pushed down into the core tube 16 until it contacts the top of the sediment sample. The rubber plug 90 then is expanded by tightening a bolt 94 in the rubber plug 90 in order to hold the rubber plug 90 in place within the core tube 16. The rubber plug 90 provides a seal that prevents contaminants from reaching the sample through the top opening 92 and prevents any of the sediment sample from escaping the core tube 16 via the top opening 92. Moreover, the rubber plug 90 prevents the sediment sample from slumping down and mixing if the core tube is transported horizontally or upside-down.

In the preferred embodiment, the core tube 16 is further sealed against contamination by fitting a rubber bottom cap 96 onto the bottom end 86 and a rubber top cap 98 onto the top end 65 of the core tube 16. It is possible to seal the sediment sample from contact with air (a requirement of certain types of chemical analysis) by installing the bottom cap 96 while the core tube 16 is under water. The top of the sediment sample is protected from contact with air by water retained inside the core tube 16 on top of the sediment sample. Then rubber plug 90 and top cap 98 are installed with the water remaining on top of the sediment sample or the water can be removed before the rubber plug 90 and top cap 98 are secured.

Based on the foregoing discussion, it will be appreciated that by vibrating a core tube while driving the core tube in a body of earth material, the preferred embodiment of the present invention enables samples of earth materials to be collected quicker and more efficiently than with prior art sampling devices. In addition, by not being rigidly attached to a sampling vessel, the preferred embodiment of the invention can be deployed under obstacles such as floating piers. Moreover, by vibrating the core tube while extracting the core tube from the earth material being sampled, the preferred embodiment enables the core tube to be extracted more easily than when using prior art samplers.

It should be understood that even though numerous advantages of the present invention have been set forth in the foregoing description of a preferred embodiment, the above disclosure is illustrative only. Changes may be made in detail and yet remain within the broad principles of the present invention. As such, the method and apparatus of the present invention are defined by the claims which follow and are not limited to the preferred embodiment described herein.

We claim:

1. An apparatus for collecting a sample of sediment, comprising:

a sample container having an end with an opening for receiving the sample;

a linear driver coupled to the sample container, the linear driver driving the sample container into the sediment with a linear force directed in a first direction toward the sediment;

a vibrator coupled to the sample container, the vibrator reciprocally driving the sample container back and forth transversely to the first direction while the linear driver drives the sample container into the sediment to collect the sample in the sample container; and an airbag coupled to the linear driver, the airbag supporting the linear driver, vibrator, and sample container when the apparatus is used under water, the airbag being controlled by an air intake valve and an air exhaust valve to alter the buoyancy of the airbag as desired.

2. The apparatus of claim 1 wherein the sample container includes a door that releasably covers the opening, the door being configured to automatically open while the sample container is being driven into the sediment and automatically close while the sample container is being removed from the sediment, the door having an end portion bent inwardly when the door is open such that when the sample container contains the sample and is removed from the sediment, the sample pushes downward on the end portion to close the door.

3. The apparatus of claim 1 wherein the opening is defined by a rim and the sample container includes a door pivotally coupled to the rim, the door being shaped to enable the door to lay against an inside wall of the sample container when the door is pivoted inwardly to allow the sediment to enter the sample container.

4. The apparatus of claim 1 wherein the linear driver includes a pneumatic motor that forces the sample container unidirectionally toward and into the sediment.

5. The apparatus of claim 1 wherein the linear driver includes a pneumatic motor that forces the sample container toward and into the sediment, the apparatus further including an exhaust line extending from the linear driver through the water to air located above the water such that gas from the linear driver is released to the air without mixing with the water.

6. The apparatus of claim 1 wherein the linear driver includes a reciprocating piston that transmits a pulsed, linear driving force to the sample container to drive the sample container into the sediment.

7. The apparatus of claim 1 wherein the end is a first end opposite to a second end of the sample container and the sample container includes a door that releasably closes the first end and an expandable sealing plug positioned inside the sample container between the sample and the second end, the sealing plug being structured to have an unexpanded cross-sectional area that enables the sealing plug to slide within the sample container and an expanded cross-sectional area that enables the sealing plug to retain the sample in position against the door and create a seal between the sample and the second end.

8. The apparatus of claim 1, further including a connecting plate affixed to and extending downward from the linear driver and into a top end of the sample container, wherein the vibrator includes a vibrator motor and a flange coupled to the connecting plate in a manner that transfers vibrations from the vibrator motor to the sample container via the connecting plate.

* * * * *